United States Patent [19]

Travers et al.

[11] Patent Number: 4,923,835
[45] Date of Patent: May 8, 1990

[54] CATALYST OF ALUMINOSILICATE TYPE CONTAINING AT LEAST ONE NOBLE METAL AND ITS USE FOR ISOMERIZING A C8 AROMATIC CUT

[75] Inventors: Christine Travers; Francis Raatz, both of Rueil Malmaison; Jean-Louis Guth, Mulhouse; Henri Kessler, Wittenheim, all of France

[73] Assignee: Institut Francais du Petrole, Rueil-Malmaison, France

[21] Appl. No.: 235,342

[22] Filed: Aug. 12, 1988

[30] Foreign Application Priority Data

Aug. 14, 1987 [FR] France ................. 87 11634

[51] Int. Cl.$^5$ .......................... B01J 29/06; B01J 29/32
[52] U.S. Cl. ....................................... 502/66; 502/68; 502/74
[58] Field of Search ............................. 502/66, 68, 74

[56] References Cited

U.S. PATENT DOCUMENTS 4,542,117 9/1985 Morris et al. ............... 502/66
4,588,701 5/1986 Chiang et al. ............... 502/68

FOREIGN PATENT DOCUMENTS 201856 11/1986 European Pat. Off. ........... 502/66

OTHER PUBLICATIONS

Kessler et al., "N.m.r. and i.r. study of B and B-Al Substitution in Zeolites of the MFI-Structure Type Obtained in Non-Alkaline Fluoride Medium", Zeolites, 1987, vol. 7, Jul., pp. 360-366.

Meier et al., Atlas of Zeolites Structure Types, 1987, pp. 100-101 and 88-89.

Primary Examiner—Carl F. Dees
Attorney, Agent, or Firm—Millen, White & Zelano

[57] ABSTRACT

Catalyst of aluminosilicate type for isomerization of a C8 aromatic cut, characterized by the following composition, expressed by weight:
(a) 0.01 to 1.5% of at least one metal selected from platinum and palladium,
(b) 0 to 99.49% of a matrix,
(c) 0.5 to 99.99% of a zeolite corresponding to the following approximate formula:

$M_{2/n} O, Al_2O_3, X SiO_2,$ wherein
M is a proton and/or a metal cation,
n is the valence of said cation,
x is a number from 12 to 1000, the zeolite, of MFI structure, synthesized in fluoride medium, containing a fluorine proportion, incorporated therewith during the synthesis, in the range from 0.02 to 1.5% by weight.

8 Claims, 1 Drawing Sheet

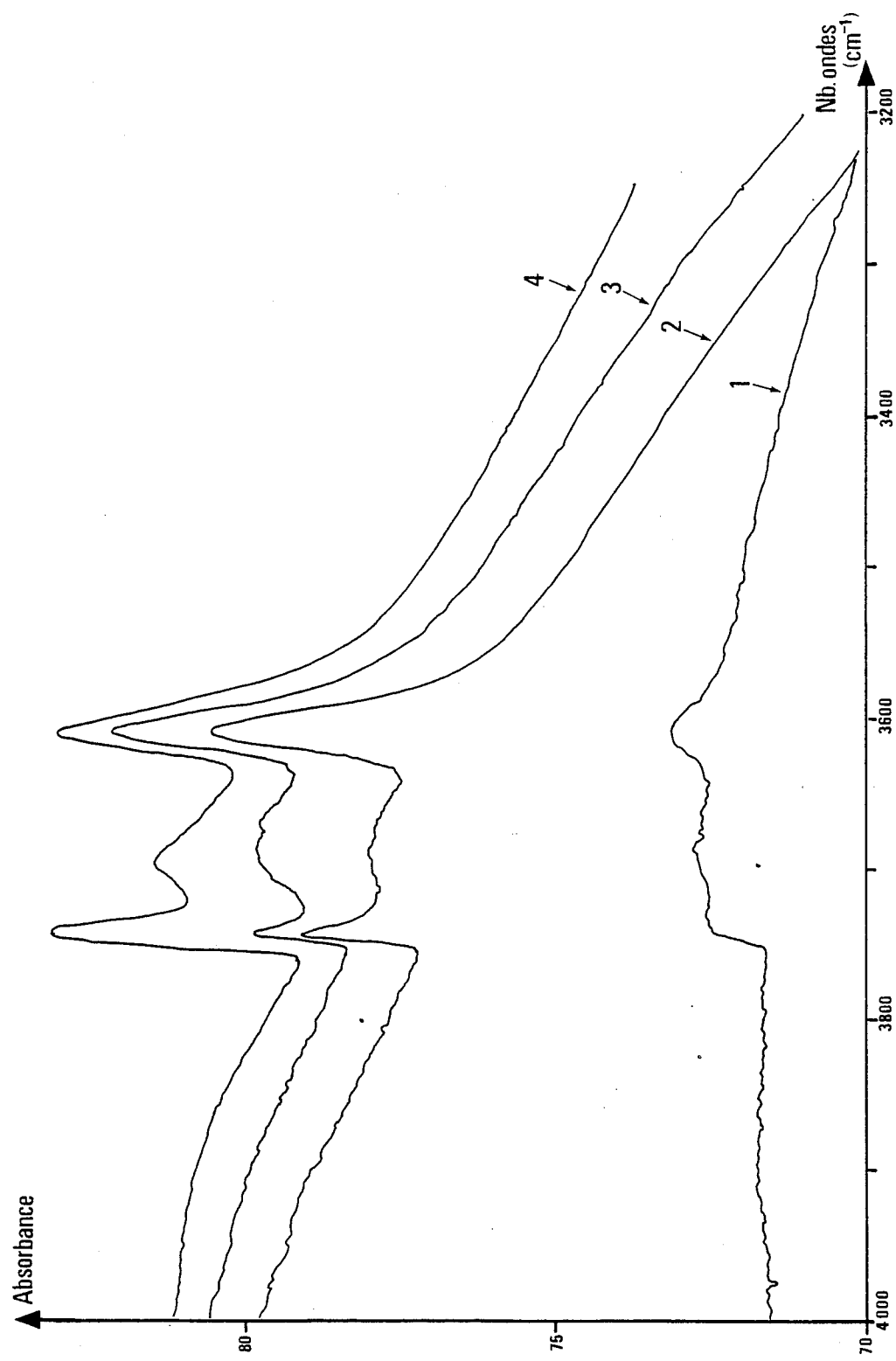

CATALYST OF ALUMINOSILICATE TYPE CONTAINING AT LEAST ONE NOBLE METAL AND ITS USE FOR ISOMERIZING A C8 AROMATIC CUT

The present invention concerns:
a catalyst of aluminosilicate type comprising a zeolite of MFI structure, containing silicium and aluminum, synthesized in fluoride medium and a group VIII metal, and
the use of said catalyst for isomerizing $C_8$ aromatic hydrocarbons.

BACKGROUND OF THE INVENTION

The prior art is illustrated in particular by the following patents:
USP 3 791 963, FR 1 510 253, EP 70 657, EP 31 255 and DE 1 542 559.

The synthesis is fluoride media of this type of zeolite of MFI structure has already been disclosed in the French patent 2 567 868 and more recently in an article of J.L.GUTH and coll. (Proc. 7th Int. Zeolite Conf, Tokyo, August 1986, p. 121).

This synthesis comprises:

(a) a first step of forming a reaction medium comprising water, a silica source, an alumina source, a source of structurizing agent for supplying organic cations selected from the group consisting of tetrapropyl ammonium(TPA+) and tetrapropylphosphonium (TPP+) cations, this reaction medium further containing fluoride anions. The pH of the medium is generally lower than 10 and the molar ratios of the various constituents of the reaction medium are disclosed in French patent 2 567 868.

(b) a second step of heating the reaction medium formed in step (a) at a temperature ranging from about 80° to 230° C., preferably from 140° to 210° C., so as to obtain a crystallized solid which is separated, (c) a third step of heating the solid obtained at the end of step (b) at a temperature higher than 400° C., so as to remove, by decomposition and optionally by combustion if the treatment is performed in the presence of oxygen, the organic species supplied by the structurizing agent and contained in the solid after synthesis.

The reaction medium pH lower than 10 may be obtained either directly from one or more products forming the reaction medium, or by adding to said medium an acid, a base, an acid salt, a basic salt or a complementary buffer mixture.

Fluoride anions $F^-$ may be introduced into the reaction medium as fluorides, sodium fluoride NaF, ammonium fluoride $NH_4F$, acid ammonium fluoride $NH_4HF_2$, tetraproprylammonium flouride $(C_3H_7)_4NH$, tetrapropylphosphonium fluoride $(C_3H_7)_4PF$, or hydrolyzable compounds capable of releasing fluoride anions in water, such as silicon fluoride $SiF_4$ or sodium fluorisilicate $Na_2SiF_6$.

Ammonium flouride or acid ammonium fluoride are preferred since they result in a zeolite of MFI structure, easy to convert to its protonic form without requiring ion exchange reactions.

Many silica sources can be used to form the reaction mixture, such as for example :

silicas as hydrogels, aerogels, colloidal suspensions,
silicas obtained by precipitation of soluble silicate solutions, or by hydrolysis of silicic esters such as tetraethyl ester of monoorthosilicic acid $Si(OC_2H_5)_4$, or complexes such as sodium fluorosilicate $Na_2SiF_6$ or ammonium fluorosilicate $(NH_4)_2SiF_6$, silicas prepared by extraction and activation of natural or synthetic crystallized compounds such as aluminum silicates, aluminosilicates, clays, etc... The silicas may be used in divided state or as agglomerates.

Examples of alumina sources are aluminum salts (sulfate, nitrate chloride, fluoride, acetate, for example), aluminum hydroxides and oxides, aluminates, esters such as tripropylester of monoorthoaluminic acid Al-$(OC_3H_7)_3$.

Instead of separate alumina and silica sources, combined sources of both oxides, such for example as amorphous silicaalumina gels, crystallized aluminosilicates, comprising clays and zeolites, can also be used.

The silica and alumina sources may be in soluble or solid form, but also in the form of agglomerates such as extrudates or pellets. Pellets are convenient for sources consisting essentially of raw zeolites or already agglomerated modified zeolites, which may be thus converted by the new process to preformed zeolites.

The sources of struturizing agent supplying organic cations are preferably tetrahydrocarbylammonium and tetrahydrocarbylphosphonium cations, whose hydrocarbyl group is advantageously an alkyl, preferably a propyl group.

Tetrapropylammonium (TPA+) or tetrapropylphosphonium (TPP+) cations, which are the preferred structurizing agents, are preferably added as salts, for example as bromides or fluorides, but they may also be generated in situ from tripropylamine or tripropylphosphine and a propyl halide.

The acids or acid salts, the bases or basic salts optionally added to bring the pH of the reaction medium to the desired value may be selected from usual acids, such as hydrofluoric acid HF, hydrochloric acid HCl, nitric acid $HNO_3$, sulfuric acid $H_2SO_4$, acetic acid $CH_3COOH$, or acid salts such as acid ammonium fluoride $NH_4HF_2$, acid potassium fluoride $KHF_2$, acid sodium sulfate $NaHSO_4$, acid potassium sulfate $KHSO_4$, acid sodium phosphate $NaH_2PO_4$ and from usual bases, such as ammonia $NH_4OH$, sodium hydroxide NaOH, potassium hydroxide KOH, or usual basic salts such as sodium acid carbonate $NaHCO_3$ or neutral carbonate $Na_2CO_3$, sodium acetate $CH_3COONa$, sodium neutral or acid sulfides ($Na_2S$ or NaHS) or buffer mixtures such as acetic acid $CH_3COOH$-sodium acetate $CH_3COONa$, ammonia $NH_4OH$-ammonium chloride $NH_4Cl$.

The morphology, the size and the kinetics of formation of zeolite crystals according to the process of the invention may be modified by introducing into the reaction medium complementary salts such as sodium chloride NaCL, potassium chloride KCl, sodium sulfate $Na_2SO_4$ and/or crystals (crushed or not) or solid compounds related to the zeolites prepared by the process of the invention.

TABLE 1

| X-ray spectrum characteristics of zeolites of MFI structure according to the invention | | | | | |
|---|---|---|---|---|---|
| $d_{hkl}$ (Å) | $I/I_o$ | $d_{hkl}$ (Å) | $I/I_o$ | $d_{hkl}$ (Å) | $I/I_o$ |
| 11.08–11.26 | VS | 4.06–4.10 | vl | 2.772–2.793 | vl |
| 9.94–10.20 | ml | 3.99–4.05 | l | 2.725–2.749 | vl |
| 9.68–9.90 | l | 3.83–3.89 | S | 2.677–2.697 | vl |
| 8.98–9.08 | vl | 3.80–3.86 | m | 2.648–2.670 | vl |
| 8.00–8.09 | vl | 3.74–3.78 | ml | 2.605–2.619 | vl |
| 7.40–7.52 | vl | 3.70–3.74 | ml | 2.581–2.597 | vl |
| 7.03–7.22 | vl | 3.63–3.67 | ml | 2.545–2.557 | vl |
| 6.64–6.84 | l | 3.58–3.62 | vl | 2.508–2.526 | vl |

TABLE 1-continued

X-ray spectrum characteristics of zeolites of MFI structure according to the invention

| $d_{hkl}$ (Å) | $I/I_o$ | $d_{hkl}$ (Å) | $I/I_o$ | $d_{hkl}$ (Å) | $I/I_o$ |
|---|---|---|---|---|---|
| 6.30–6.42 | l | 3.46–3.50 | vl | 2.479–2.501 | vl |
| 5.95–6.07 | l | 3.42–3.46 | l | 2.407–2.419 | vl |
| 5.67–5.79 | l | 3.38–3.42 | vl | 2.393–2.401 | vl |
| 5.54–5.61 | l | 3.33–3.37 | l | 2.326–2.340 | vl |
| 5.32–5.42 | vl | 3.29–3.33 | vl | 2.314–2.332 | vl |
| 5.10–5.23 | vl | 3.23–3.27 | vl | 2.195–2.209 | vl |
| 5.01–5.08 | l | 3.16–3.20 | vl | 2.104–2.120 | vl |
| 4.95–5.03 | l | 3.12–3.16 | vl | 2.077–2.095 | vl |
| 4.84–4.93 | vl | 3.08–3.12 | vl | 2.070–2.084 | vl |
| 4.59–4.64 | vl | 3.03–3.07 | l | 2.004–2.022 | l |
| 4.44–4.50 | vl | 2.976–3.020 | l | 1.985–2.005 | l |
| 4.34–4.40 | l | 2.943–2.962 | l | 1.944–1.964 | vl |
| 4.23–4.29 | l | 2.855–2.881 | vl | 1.907–1.922 | vl |
|  |  |  |  | 1.866–1.881 | vl |

VS = very strong;
S = strong; mS = middle to strong;
m = middle;
ml = middle to low;
l = low;
vl = very low The solids obtained by the above-described synthesis procedure are zeolites of MFI structure whose X-ray diffraction diagrams have characteristics corresponding to the specifications of table 1. These zeolites of MFI structure approximately conform, after roasting, to the following chemical formula, expressed as oxides:

$$M_{2/n}O, Al_2O_3, xSiO_2$$

wherein x may vary from 12 to 1,000 and M represents one or more compensation cation(s) of valence n. These solids must essentially contain, after the synthesis step and also after the step of removing organic compounds, fluorine. The zeolite fluorine content, determined by elemental analysis, is, for the roasted solids, i.e. those resulting from the above-described step (c), from 0.02 to 1.5% by weight, advantageously from 0.1 to 1.0 % and preferably from 0.2 to 0.8%.

The presence of fluorine in zeolites of MFI structure prepared according to the invention confers properties to these solids, particularly acid properties and ion exchange properties, completely different from those of zeolites of MFT structure synthesized in a conventional manner, i.e. in alkaline medium (for example USP 3 702 886). After synthesis and removal of the organic compound by roasting (steps a, b, c), the solids according to the invention are characterized by an infra-red vibration spectrum comprising, as shown in the figure for fluorine contents of 0.8% (curve 1) 0.2% (curve 2) and 0.05% (curve 3), bands conventionally attributed to Si-OH groups (3730 - 3750 cm$^{-1}$ area) and to Al-OH structural groups (3580-3640 cm$^{-1}$ area) of low intensity as compared with those of a zeolite of conventional MFI structure, having the same Si/Al ratio equal to 22 (curve 4, F %=0).

The absence or quasi absence of Al—OH structural groups in the zeolites according to the invention is confirmed by the ion exchange capacities of these solids. As a matter of fact the ion exchange capacities for cations such for example as Na$^+$, K$^+$, Ga$^{3+}$, Pt(NH$_3$)$_4^{2+}$ etc... are much lower than the total theoretical ion exchange capacities, as calculated from the aluminum content of the crystalline structure.

These solids have no or only a few structural hydroxyl groups and a very reduced exchange capacity, yet surprisingly exhibti remarkable acid properties. Thus the ammonia thermodesorption used to estimate the overall acidity of a solid (number and strength of the different types of acid sites) show that solids including fluorine incorporated with the structure are very acid. The ammonia thermodesorption spectra are similar to those obtainable with conventional zeolites of MFI structure, but the acidity of the solids according to the invention is of a different nature.

Without being bound by any particular theory, it may be considered for example that these solids have, in place of at least a part of the conventional

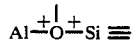

sites, sites of the following types:

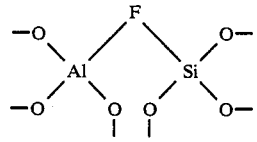

The precise nature of the acid sites present in the solids according to the invention has still to be precisely stated, but it is clear that most of these sites are associated with the presence of fluorine and differ by their nature from acid sites of conventional MFT zeolites.

Fluorine introduction into zeolites has already been proposed for increasing the acidity of said solids (S.KOWALAK, React. Kinet. Catal. Lett, 27, 1985 p. 441 and J. Chem. Soc. Farad. Trans 1, 82, (1986), 2151; J. MIALE and C. CHANG USP 4,540,841). However, in the prior art, fluorine is introduced into the zeolite through modifications achieved after synthesis. Otherwise stated, a conventional synthesis, i.e. in alkaline medium, is first achieved, and then the solid is treated by a technique known as adapted to fix fluorine. These above-proposed techniques generally suffer from heavy defects. For example, as when treating the solid with fluorine gas, they are liable to result in a degradation of the crystalline order (USP 4,297,335). In the present catalyst preparation, fluorine is introduced into the zeolite during the synthesis and gives, on the contrary, very well crystallized solids.

By particular treatments it is possible to partially or completely remove fluorine from the solids involved in the composition of the catalysts according to the invention without modifyin their crystallinity. A technique for defluorinating the solids comprises treatment in ammonia solution within a temperature range from room temperature to 200° C., for example (treatment in autoclave under autogenic pressure). The partial or complete fluorine removal has as a result:

the formation in the IR spectrum of two bands located about at 3740 and 3608 cm$^{-1}$, corresponding, according to the scientific literature, respectively to ending silanol groups and structural Al-OH groups, and the restoration of the ion exchange capacity, as determinable by the aluminum content of the solid structure.

Thus, depending on the defluorination treatment, solids containing a variable amount of Al—OH and Si—OH groups, and having a variable ion exchange capacity, can be obtained for the same Si/Al ratio of structure. A partially defluorinated solid hence contains, in addition to conventional acid sites of Al-OH type, which may act as exchange sites, particular acid sites, whose exact nature is still not completely known, but which undenisably result from the fluorine introduction in the solids during the synthesis.

By taking advantage of this particularity of the solids it has been possible to prepare bifunctional catalysts containing at least one group VIII metal selected from platinum and palladium and for example adapted for isomerization of a $C_8$ aromatic hydrocarbon, more generally of a $C_8$ aromatic cut, and whose acid properties are of a new type.

SUMMARY OF THE INVENTION

Thus, the present invention concerns a catalyst of alumino-silicate type, characterized by the following composition by weight:

(a) 0.01-1.5% of at least one metal selected from platinum and palladium, (b) 0-99.49% of a matrix selected from the group formed of alumina, silica, magnesia, a clay or any combination of at least two of the above-mentioned compounds, and (c) 0.50-99.99% of a zeolite synthesized in fluoride medium, having a $SiO_2/Al_2O_3$ molar ratio from 12 to 1000, the zeolite fluorine content being from 0.02 to 1.5%, fluorine being incorporated during the synthesis, said zeolite being also characterized by a X-ray diffraction diagram as shown in table 1.

Generally, the zeolite has approximately the following formula:

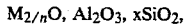, $Al_2O_3$, $xSiO_2$, wherein:

M is a proton and/ro a metal cation, n is the cation valence x is a number from 12 to 1000

After synthesis in fluoride medium, the solid may be subjected, if necessary, to a defluorination treatment for adjusting its ion exchange capacity to the group VIII metal content to be deposited. The lower the fluorine content, the higher the possible platinum or palladium content.

The defluorination treatment is more or less severe depending on the desired defluorination extent. It consists in one or more successive treatments of the solid, at reflux in an ammonia solution of normality from about 0.05 to 5 N, preferably from 0.1 to 3 N, for about 0.5-5 hours, preferably 1-4 hours with a V/W ratio, defined as ratio of the solution volume in proportion to the weight of dry solid, ranging from about 5 to 50 cc.g$^{-1}$, preferably from 10 to 30 cc.g$^{-1}$. The solid, after each washing, is then further washed extensively with distilled water and dried in a stove. After these treatments, and depending on their severity, the fluorine content of the solid ranges from 0.9 to 0.01 % by weight. The solids obtained by removing, by repeated treatments, substantially all the fluorine, are different, in particular by their IR spectrum in the 3800-3500 cm$^{-1}$ area, from zeolites of conventional MFI type having the same Si/Al ratio of structure: the solids contained in the catalyst according to the invention comprise a higher proportion of Si—OH groups.

The partially or completely defluorinated solid may be subjected as such to deposition of the group VIII metal or shaped by any technique known in the art. By group VIII metal it is meant platinum and palladium. In particular, it may be admixed to a generally amorphous matrix, for example an alumina gel moist powder. The mixture is then shaped, for example by extrusion through a drawing-plate. The zeolite content of the obtained carrier is generally from about 0.5 to 99.99 %, advantageously from 40 to 90 % and more particularly from 60 to 85 % by weight, in proportion to the whole zeolite and matrix amount.

The matrix content of the catalyst is advantageously from about 10 to 60%, preferably from about 15 to 40 % by weight. The shaping may be performed with other matrices than alumina, such for example as magnesia, silica-alumina and natural clays (kaolin, bentonite) and by using other techniques than extrusion such as pelletizing or bowl-granulation. The group VIII hydrogenating metal, preferably Pt or Pd, is then deposited onto the carrier by any process known in the art for metal deposition onto zeolite. The cation exchange technique with competition, where the competitor agent is preferably ammonium nitrate and the competition ratio at least equal to 50 and advantageously from 50 to 150, can be used. Platinum or palladium, are used respectively as a platinum tetrammine complex or a palldatium tetrammine complex. The latter will then deposit practically entirely onto zeolite. This cation exchange technique may also be used to directly deposit platinum onto zeolite powder, before its eventual admixture with a matrix. The metal deposition is followed with a roasting under air or $O_2$ for 0.5 to 10 hours at a temperature from 300° to 600° C., preferably from 350° to 500° C., for 1–4 hours. Then, a reduction is performed under hydrogen at a temperature from 300° to 600° C. for 1-10 hours, preferably at 350°-550° C. for 2-5 hours. The group VIII metal (Pt or Pd) amount deposited onto the catalyst and obtained at the end of the exchange depends on the defluorination rate of the solid. It ranges from 0.01 to 1.5% preferably from 0.03 to 0.4% by weight in proportion to the whole catalyst weight.

In order to deposit, irrespective of the fluorine content, the desired platinum or palladium amount, the latter, instead of being directly deposited onto the zeolite, may be deposited advantageously onto the aluminum binder, before or after the shaping step, by anion exchange with hexachloroplatinic acid, hexachloropalladic acid or palladium chloride in the presence of hydrochloric acid as competitor agent. It is thus always possible to deposit up to 0.5%, preferably from 0.03 to 0.4% by weight of platinum. After platinum deposition, the catalyst, as precedingly, is subjected to roasting at 300°–600° C. and then reduced under hydrogen, as above-indicated. By this latter procedure zeolite may be used in completely fluorinated form and it is possible to deposit a metal amount higher than the zeolite exchange capacity, which may reach 1.5 % by weight of the catalyst.

The bifunctional catalyst obtained by the preceding procedures is used for example for isomerization of a $C_8$ aromatic cut comprising either only a mixture of xylenes, or a mixture of xylenes and ethylbenzene. The isomerization of alkyl aromatics, particularly of xylenes, is of high commercial importance. Ortho and paraxylene are the more useful products, paraxylene in particular as intermediate in the manufacture of polyester fibers, orthoxylene mainly for the preparation of phthalic anhydride. Metaxylene, or less industrial interest, is advantageously converted by isomerization to ortho and paraxylene. Ethylbenzene, difficult to separation from the xylene mixture, (the boiling points of the different components are very close to one another) is often present in the $C_8$ aromatic isomerization charge.

EXAMPLES

The following examples are given to further illustrate the invention without however limiting the scope thereof. They relate to a charge formed only of metaxylene but are easily transposable to a more complex charge essentially comprising metaxylene and ethylbenzene.

With an ethylbenzene charge, the conversion mechanism is an acid bifunctional mechanism involving the formation of dehydrogenated intermediates requiring the presence of a group VIII metal for the hydrogenating/dehydrogenating function. For a charge comprising only xylenes, the isomerization mechanism is essentially an acid mono functional mechanism, but the presence of a hydrogenating metal is necessary for the stability and even for the selectivity of the catalyst.

EXAMPLE 1

Preparation of A and B zeolites used as components of the catalyst according to the invention Two zeolites of MFI structure, having Si/Al atomic ratios of about 20 and 250 respectively, are prepared from the same aluminum and silicon source, consisting of partially dealuminated Tixolex 28, but with two different F/Si atomic ratios in the two reaction mixtures.

Tixolex 28 is a sodium aluminosilicate sold by Rhône-Poulenc and characterized by the atomic ratios : Si/Al =78.3 and Na/Al =1.1. The partially dealuminated form is prepared as follows: 60 g of Tixolex 28 are stirred for 3 hours at room temperature with 600 ml of $HNO_3$ M/2. The obtained product is filtered and washed with water up to a pH of 7. After drying at 80° C., it is kept in relative moistness of 80 %. It contains by weight: 76.10 % $SiO_2$, 5.46 % $Al_2O_3$, 0.25 % $Na_2O$, 17.63 % $H_2O$.

Two reaction mixtures A and B are prepared, whose compositions by mole and by weight are indicated in table 2. For this preparation, the mixture of $NH_4F$, $N(C_3H_7)_4{}^+Br^-$ and water is added to the partially dealuminated Tixolex, under stirring. The two reaction mixtures A and B are crystallized in two autoclaves, innerly coated with polytetrafluoroethane, at 190° C. for 3.5 days.

TABLE 2

| | Partially dealuminated Tixolex | | | | |
|---|---|---|---|---|---|
| | $SiO_2$ | $Al_2O_3$ | $NH_4F$ | $N(C_3H_7)_4Br$ | $H_2O$ |
| A | | | | | |
| moles | 0.2 | 0.0084 | 0.04 | 0.1 | 1.6 |
| g | | 15.8 | 1.48 | 26.6 | 28.8 |
| B | | | | | |
| moles | 0.2 | 0.0084 | 0.25 | 0.1 | 1.6 |
| g | | 15.8 | 9.25 | 26.6 | 28.8 |

After crystallization, the solids are filtered and washed with a 10 % diethylamine solution, then with a hot water solution. The solids are then dried at 80° C. Crystallography analysis shows that products A and B are zeolites of MFT structure whose X-ray diffraction diagram corresponds to the specifications of table 1. The chemical analysis of products A and B, after roasint in air at 550° C., is as follows:

| Products | A | B |
|---|---|---|
| Si/Al atomic ratio | 22 | 240 |
| F (% by weight) | 0.8 | 0.5 |

EXAMPLE 2

Catalyst B1 conforming with the invention

Solid B of example 1 is shaped by extrusion with a binder of aluminic type, in a proportion by weight of 80 % zeolite and 20 % binder. The group VIII metal, here platinum, is deposited onto the extrudates by ion exchange with competition. The platinum salt is the Keller complex Pt $(NH_3)_4$ $Cl_2$ and the competitor agent is $NH_4NO_3$. The competition ratio $NH_4{}^+/2$ $Pt(NH_3)_4{}^{2+}$ is about 50. Platinum deposition is followed with a roasting in air at 450° C. for 2 hours. The obtained catalyst is referenced B1.

Starting solid B having a high fluorine content (0.5 % by weight), the platinum content obtained by exchange is rather low. The platinum content of catalyst B1 is 0.06 % by weight. The X-ray diffraction spectrum is substantially similar to that of example 1. Catalyst B1 is tested for metaxylene isomerization at a temperature of 400° C., a pressure of 15 bars, a molar $H_2$ / metaxylene ratio of 4 and a space velocity (wwh) of 3.6. The catalytic performances are reported in table 3.

They are defined by:

m-xylene conversion (%) =

$$\frac{\text{m-xylene input weight} - \text{m-xylene output weight}}{\text{m-xylene input weight}} \cdot 100$$

Selectivity to isomerization =

$$\frac{\text{o-xylene weight} + \text{p-xylene weight}}{\text{weight of products}} \cdot 100$$

Approach to p-xylene balance =

$$\frac{\text{number of p-xylene moles at output}}{\text{number of p-xylene moles at thermodynamic balance}}$$

Isomerization yield = $\frac{\text{conversion} \times \text{selectivity}}{100}$

Yield to $C_8$ aromatics = $\frac{\text{weight of } C_8 \text{ aromatics at output} \times 100}{\text{total weight of } C_8 \text{ aromatics at input}}$

EXAMPLE 3

Catalyst B2 conforming with the invention

Solid B of example 1 is subjected to a defluorination step consisting of bringing the solid to reflux for 4 h in a 0.2 N ammonia solution, with a ratio of solution volume to dry solid weight of 20 cc $g^{-1}$. The solid is then washed extensively with distilled water and then again suspended for performing a second exchange. After filtration and washing, the solid is dried in stove at 120° C. Its fluorine content is then 0.10 %. The solid is then shaped by extrusion in the same conditions as catalyst B1 and platinum is deposited, by competitive exchange, as above-described in example 2. However, the exchange capacity after defluorination being multiplied by a factor of about 4, the amount of Keller complex to introduce is so adjusted as to obtain a platinum content equivalent to that of catalyst B1 (0.06%). After platinum deposition, the catalyst is roasted in air and reduced under hydrogen in the conditions of example 2. The obtained catalyst is referenced B2.

The performances of this catalyst, tested for isomerization in the conditions of example 2, are reported in table 3. They indicate a lower selectivity to isomerization and a lower yield to $C_8$ aromatics than with catalyst B1 of higher fluorine content and identical metal content.

EXAMPLE 4

Catalyst B3 conforming with the invention

Catalyst B3 differs from catalyst B2 by an attempt to obtain a substantially complete defluorination. Accordingly, the defluorination step is more severe than in example 3. Four successive treatments are conducted in the following conditions: the solid is brought to reflux for 4 h in a 1.5 N ammonia solution, with a ratio of solution volume to dry zeolite weight of 20 cc g$^{-1}$. Between two successive treatments, the solid is extensively washed with distilled water and then again brought in suspension. After the last washing, the solid is dried in stove at 120° C. Its fluorine content is then 0.02 %. After defluorination, the solid is shaped in the conditions of example 2. The zeolite having recovered substantially its whole exchange capacity (calculated with respect to the Al content of the struture), the platinum amount to introduce is so adjusted as to obtain a Pt content of the final catalyst equivalent to that of catalysts B1 and B2. Platinum deposition is performed according to the method described in example 2. After platinum deposition, the catalyst is roasted in air and reduced under hydrogen in the conditions of example 2. The obtained catalyst is referenced B3. Its catalytic performances for isomerization in the conditions of example 2 are given in table 3.

EXAMPLE 5

Comparison catalyst C

Catalyst C is a zeolite of MFI structure, synthesized in conventional basic medium, as described in USP 3,702,886. This zeolite is synthesized with a Si/Al ratio of 240 and is completely free of fluorine after synthesis. Platinum is deposited according to the method described in example 2. The platinum content is equivalent to that of catalyst B1, B2, B3. This catalyst is shaped and activated in the conditions of example 2. The tested performances of catalyst C for isomerization in the conditions of example 2 are reported in table 3. It is observed that these performances are lower than those of catalyst B1 conforming with the invention. They are however close to those of catalyst B3, i.e. of the catalyst conforming with the invention which is substantially free of fluorine.

EXAMPLE 6

Catalyst A1 conforming with the invention

A catalyst is prepared in the conditions described in example 2, but with the use of zeolite A of example 1 whose Si/Al atomic ratio is 22. The obtained catalyst, referenced A1, is tested in the same conditions as the preceding catalysts. The catalytic performances of catalyst A1, tested for isomerization according to the conditions of example 2, are reported in table 3. The fluorine content is 0.80 % by weight. The platinum content is 0.06 % by weight.

EXAMPLE 7

Catalyst A2 conforming with the invention

Catalyst A2 differs from catalyst A1 in that, before extrusion, the zeolite is partially defluorinated.

Defluorination is performed in two successive treatments in a solution of NH$_4$OH 0.25N, at 80° C. for 2 hours. After each treatment the solid is filtered and extensively washed with distilled water. After the last washing, it is dried in a stove at 120° C. Its fluorine content is then 0.2 % by weight. The platinum content is adjusted to the same value as for the other catalysts, i.e. 0.06 % by weight. After platinum deposition, the catalyst is roasted in air and reduced in the same conditions as in example 2. The obtained catalyst is referenced A2. Its catalytic performances for isomerization, tested in the conditions of example 2, are reported in table 3.

EXAMPLE 8

Comparison catalyst D

A zeolite of MFI structure and Si/Al ratio of 22 is synthesized in conventional medium, in accordance with the process of USP 3 702 686. This zeolite does not contain any fluorine.

0.06 % by weight of platinum are deposited on said carrier shaped as in example 2, by cation exchange. Catalyst D is activated and tested in the above-stated conditions (example 2). Its catalytic performances are reported in table 3.

EXAMPLE 9

Comparison catalyst F

A zeolite of MFI structure and Si/Al ratio of 240 is synthesized in conventional medium according to the procedure disclosed in USP 3 702 886. This zeolite is subjected to a roasting step of 550° C., followed with three exchanges in NH$_4$NO$_3$ 3N. The solid is then subjected to a treatment at 450° C. under a CHF$_3$-containing atmosphere for 4 hours. The fluorine content at the end of this treatment reaches 0.15 % by weight. This solid is then shaped, subjected to a cation exchange so as to deposit 0.06 % by weight of platinum, and then to a roasting and to a reduction in the conditions described in example 2. The catalyst performances of the prepared catalyst F, tested for isomerization in the conditions of example 2, are reported in table 3. It appears that the performances of catalyst F are lower than those of catalyst B2 according to the invention, whose Si/Al ratio and fluorine content are close to those of catalyst F.

EXAMPLE 10

Catalyst B4 conforming with the invention.

Catalyst B4 differs from catalyst B1 of example 2 in that platinum, instead of being deposited onto zeolite, is deposited onto alumina by ion exchange with hexachloroplatinic acid. The catalyst platinum content is 0.06 %. Its fluorine content is 0.5 %. Platinum deposition, as precedingly, is followed by a roasting step in air at 500° C. for 2 hours and by a reduction in situ at 450° C. for 2 hour. The performances of this catalyst, referenced B4, after 10 hours of run, are reported in table 3. They are quite similar to the performances of catalyst B1. The performances of catalyst B4, after 100 hours of run, are reported in table 4.

EXAMPLE 11

Catalyst B5 conforming with the invention

Catalyst B5 differs from catalyst B4 of example 10 in that it contains 0.3 % platinum, which is still deposited by anion exchange so that the total platinum amount be deposited onto alumina. This catalyst, referenced B5, is subjected to the thermal treatments described in example 10. Its performances after 10 hours of run are reported in table 3, and after 100 hours of run in table 4. In contrast to catalyst B4 of low platinum content, the performances of catalyst B5 are much more stable during time.

EXAMPLE 12

Catalyst B0, not conforming with the invention.

Catalyst B0 differs from all of the above-described catalysts in that it does not contain platinum at all. It is tested for m-xylene isomerization, directly after shaping. Its performances after 100 hours of run are reported in table 4. They are not measurable: the catalyst is completely deactivated.

EXAMPLE 13

Catalyst B6 conforming with the invention

Catalyst B6 differs from catalyst B1 of example 2 in that the deposited group VIII metal is not platinum but palladium.

0.06% by weight of palladium are deposited from palladium chloride in the presence of hydrochloric acid as competitor agent. The obtained catalyst is then roasted in air at 500° C. for 2 hours and reduced in situ at 450° C. for 2 hour. Its performances for m-xylene isomerization are reported in table 3. They are substantially similar to those of catalyst B1.

TABLE 4

| Comparison of different catalysts after 100 hours of run | | | |
|---|---|---|---|
| Catalyst | B0 | B4 | B5 |
| Si/Al atomic ratio | 240 | 240 | 240 |
| F % | 0.5 | 0.5 | 0.5 |
| Pt % | 0 | 0.06 | 0.3 |
| m-xylene conversion % | 0 | 45 | 48 |
| Isomerization selectivity (%) | 0 | 92.8 | 95.8 |
| Approach to p-xylene balance | 0 | 100 | 100 |
| Isomerization yield (%) | 0 | 41.8 | 46.0 |
| Yield of C8 aromatics (%) | 0 | 96.5 | 98.0 |

What is claimed as the invention is:

1. An aluminosilicate catalyst comprising by weight:
   (a) 0.01 to 1.5% of at least one metal selected from platinum and palladium,
   (b) 0 to 99.49% of a matrix selected from the group formed of alumina, silica, magnesia, a clay or any combination of at least two of the above-mentioned compounds, and
   (c) 0.5 to 99.9% of a zeolite of MFI structure having a $SiO_2/Al_2O_3$ molar ratio from 12 to 1000,
      said zeolite, previously synthesized in fluoride medium at a pH lower than 10, having a fluorine content from 0.02 to 1.5% by weight, being characterized by an X-ray diffraction diagram as shown in table 1 of the description.
2. A catalyst according to claim 1, wherein the platinum content ranges from 0.03 to 0.4 %, by weight.
3. A catalyst according to claim 1, wherein the zeolite content ranges from 40 to 90 % by weight.
4. A catalyst according to claim 1, wherein the matrix content ranges from about 10 to 60 % by weight.
5. A catalyst according to claim 1, wherein the fluorine content in proportion to said zeolite ranges from 0.2 to 1 % by weight.
6. A catalyst according to claim 1, wherein the zeolite has the formula $M_{2/n}O: Al_2O_3:xSiO_2$, wherein M is a proton and/or a metal cation, n is the cation valence, and x is 12 to 1000.
7. A catalyst according to claim 1, wherein the amount of the zeolite in (C) is 40 to 90%.
8. A catalyst according to claim 1, wherein the amount of the zeolite in (c) is 60 to 85%.

TABLE 3

| Comparison of different catalysts after 10 hours of run (T° C. = 400; p (b) = 15; H2/HC = 4; wwh = 3.6) | | | | | | | | | | | |
|---|---|---|---|---|---|---|---|---|---|---|---|
| Catalyst | B1 | B2 | B3 | C | A1 | A2 | D | F | B4 | B5 | B6 |
| Si/Al atomic ratio | 240 | 240 | 240 | 240 | 22 | 22 | 22 | 220 | 240 | 240 | 240 |
| F % | 0.5 | 0.1 | 0.02 | 0 | 0.8 | 0.2 | 0 | 0.15 | 0.5 | 0.5 | 0.5 |
| m-xylene conversion % | 48 | 51.4 | 47.2 | 48.2 | 53.4 | 40.7 | 42 | 50.0 | 48.2 | 48 | 47.2 |
| Isomerization selectivity (%) | 94.0 | 83.2 | 81.1 | 81.3 | 74.7 | 71.0 | 65.3 | 82 | 94.3 | 95.8 | 96.4 |
| Approach to p-xylene balance | 100 | 100 | 100 | 100 | 100 | 87.6 | 75.6 | 100 | 100 | 100 | 100 |
| Isomerization yield (%) | 45.1 | 42.7 | 38.3 | 39.2 | 40.0 | 29.0 | 27.4 | 41 | 45.4 | 46.0 | 45.5 |
| Yield of C8 aromatics | 98.0 | 92.0 | 88.0 | 88.5 | 92.2 | 91.6 | 85.1 | 90.0 | 98.0 | 98.0 | 98.0 |